United States Patent [19]

O'Connell et al.

[11] Patent Number: 4,693,970

[45] Date of Patent: Sep. 15, 1987

[54] IMMUNOASSAY USING COMPLEMENT

[75] Inventors: James P. O'Connell, Chapel Hill; Randal A. Hoke, Carrboro; Patrick D. Mize, Durham, all of N.C.

[73] Assignee: Becton, Dickinson and Company, Franklin Lakes, N.J.

[21] Appl. No.: 747,497

[22] Filed: Jun. 21, 1985

[51] Int. Cl.$^4$ .................. G01N 33/53; G01N 33/536; G01N 33/543; C12Q 1/44
[52] U.S. Cl. .......................................... 435/7; 435/18; 435/19; 436/512; 436/518; 436/536; 436/800; 436/821; 436/825; 436/537
[58] Field of Search ............... 435/7, 18, 19; 436/512, 436/518, 524, 506, 507, 825, 522, 546, 821, 800, 808, 536, 528, 537

[56] References Cited

U.S. PATENT DOCUMENTS

| | | | |
|---|---|---|---|
| 3,654,090 | 4/1972 | Schuurs et al. | 435/7 |
| 4,130,634 | 12/1978 | Molinaro et al. | 436/828 |
| 4,138,213 | 2/1979 | Masson et al. | 436/509 |
| 4,235,960 | 11/1980 | Sasse et al. | 435/7 |
| 4,342,826 | 8/1982 | Cole | 435/7 |
| 4,463,090 | 7/1984 | Harris | 435/7 |
| 4,483,929 | 11/1984 | Szoka | 436/828 |

OTHER PUBLICATIONS

Lin et al. (1980) Journ. Biol. Chem., 255, No. 16: 7756-7762.
Medicus et al. (1980) Journ. Immunol., 125, No. 1: 390-395.
Bing, D. H. (1974) in "Methods in Enzymology", vol. 34 (Jacoby & Wilckek, eds.) Academic Press, pp. 731-746.
Alberts et al., *Molecular Biology of the Cell*, Garland Publishing Co., 1983, pp. 988-989.
Roitt, *Essential Immunology*, Blackwell Scientific Publications, 1980, p. 158.

*Primary Examiner*—Christine M. Nucker
*Assistant Examiner*—Jack Spiegel
*Attorney, Agent, or Firm*—Richard E. Brown

[57] ABSTRACT

A method for immunoassay of an analyte in a fluid includes contacting the analyte with an antianalyte to give a bound fraction. The bound fraction activates the first component of complement whereby a substrate present in the fluid is modulated to provide a detectable signal. The signal may be detected to establish the presence or absence of the analyte in the fluid, or it may be quantitatively measured to determine the concentration of the analyte in the fluid. The invention includes a kit of materials useful in performing the method of the invention.

15 Claims, 1 Drawing Figure

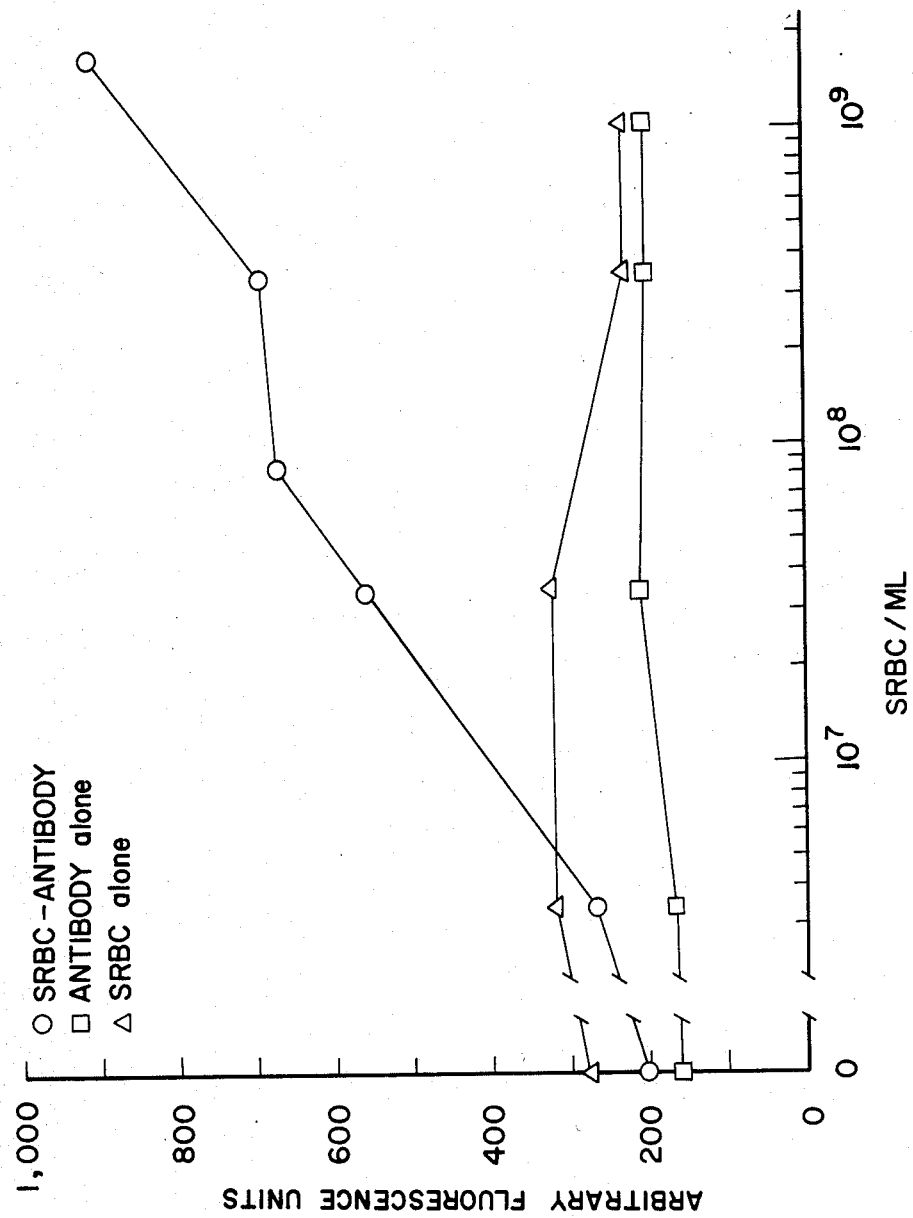

IMMUNOASSAY USING COMPLEMENT

BACKGROUND OF THE INVENTION

1. Field of the Invention.

This invention relates to immunoassay of an analyte and materials used therein, and more particularly relates to a method and materials for homogeneous immunoassay using the enzymatic activity of the first component of complement.

2. Description of the Prior Art.

A variety of assay systems which are both rapid and sensitive have been developed to determine the concentration of a substance in a fluid. Immunoassays depend on the binding of an antigen or hapten to a specific antibody and have been particularly useful because they give high levels of specificity and sensitivity. These assays generally employ one of the above reagents in labeled form, the labeled reagent often being referred to as the tracer. Immunoassay procedures may be carried out in solution or on a solid support and may be either heterogeneous or homogeneous. Heterogeneous assays require a separation of bound tracer from free (unbound) tracer. Homogeneous assays do not require a separation step and thereby provide significant advantages in speed, convenience and ease of automation over heterogeneous assays.

Radioimmunoassay (RIA) procedures use radioisotopes as labels, provide high levels of sensitivity and reproducibility, and are amenable to automation for rapid processing of large numbers of samples. However, all RIA procedures require a separation step, since the parameter measured (nuclear decay) cannot be controlled by changing assay conditions or components. In addition, isotopes are costly, have relatively short shelf lives, require expensive and complex equipment, and extensive safety measures for their handling and disposal must be followed.

Fluoroimmunoassay (FIA) uses fluorochromes as labels, provides direct detection of the label, and is readily adaptable to homogeneous assay procedures. However, known homogeneous FIA methods using organic fluorochromes, such as fluorescein or rhodamine derivatives, have not achieved the high sensitivity of RIA, largely because of light scattering by impurities suspended in the assay medium and by background fluorescence emission from other fluorescent materials present in the assay medium.

Enzymes have also been used as labels in immunoassay. In conventional enzyme immunoassay (EIA), an enzyme is covalently conjugated with one component of a specifically binding antigen-antibody pair, and the resulting enzyme conjugate is reacted with a substrate to produce a color which is measured. In U.S. Pat. No. 3,654,090 to Schuurs et al., the unconjugated component is immobilized on a solid support.

In U.S. Pat. No. 4,235,960, Sasse et al. disclose a competitive EIA in which a bound analyte-antibody complex is linked through a bridging second antibody to a third antibody carrying an immunologically attached enzyme label.

U.S. Pat. No. 4,463,090 to Harris teaches increased sensitivity in EIA by cascade amplification. In this procedure, a conjugated enzyme catalytically activates a ligand which either reacts with a substrate to produce a color or activates a second ligand to react. Two or more activation stages may be used.

U.S. Pat. No. 4,342,826 to Cole teaches an improved EIA wherein antigen-tagged liposomes containing encapsulated enzyme label are specifically bound to antibodies, and the liposomes are ruptured by active complement to release the enzyme label.

U.S. Pat. No. 4,138,213 to Masson et al. discloses detection or determination of antigens or antibodies wherein isolated complement subcomponent C1q agglomerates antibody-antigen complexes. Excess C1q in supernatent fractions is measured by addition of a second antibody-antigen complex which carries a radioactive, fluorescent or enzyme label.

SUMMARY OF THE INVENTION

One aspect of the present invention comprises a method for detecting an analyte in a fluid, or determining its concentration in the fluid wherein the first component of complement, hereinafter referred to as C1, enzymatically modulates a substrate to generate a detectable signal. An antianalyte is contacted with the analyte, and C1 and a substrate are added. The analyte binds to the antianalyte and the resulting bound fraction activates C1 to modulate the substrate to produce the signal. The method may be carried out in solution of on a solid support, and means may be provided to inhibit nonimmune activation of C1.

In a preferred embodiment of the invention, the activated C1 modulates a substrate to initiate a series of sequential reactions to provide high amplification of the detectable signal.

Another aspect of the invention includes a kit of materials for performing the method of the invention.

In accordance with the invention, a method for enzyme immunoassay for an analyte in a fluid takes advantage of the enzymatic activity of C1 to convert a substrate to a detectable signal. Because the enzyme is added to the assay medium in an inactive form and is activated only by antibody bound to antigen, unbound antibody does not activate the enzyme and does not interfere with signal generation induced by bound antibody. Thus, there is no need for separation of bound and unbound fractions. By using C1, covalent attachment of the enzyme or an enzyme-encapsulating liposome to an antigen or an antibody is avoided. Use of a substrate to initiate a sequence of reactions giving a detectable signal provides high amplification of the detectable signal by a small quantity of C1. Assay sensitivity thereby equals that of RIA in a procedure which is simple, fast, convenient and readily adaptable to automation.

BRIEF DESCRIPTION OF THE DRAWING

The FIGURE shows the results of an assay for sheep red blood cells in accordance with the method of the invention.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

Complement is a complex series of soluble serum proteins which is intimately involved in defense against invading microorganisms. It consists of about 20 sequentially interacting components designated C1,C2,C3......C9, factor B, factor D, and a variety of regulatory proteins. C1 consists of three subcomponents designated C1q, C1r and C1s. The term complement is hereinafter understood to mean the above-described series of soluble serum proteins.

In accordance with the method of the invention, a substance suspected to be present in a fluid, hereinafter referred to as the analyte, may be detected, or if desired, its concentration determined by means of an immunological reaction. By the term "immunological reaction," as used herein, is meant a specific binding reaction of an antigen and an antibody, a hapten and an antibody, or any appropriate analogue of an antigen, and antibody, or a hapten which also binds specifically, and which gives a bound fraction capable of activating C1.

The immunological reaction may be carried out in any suitable fluid. For example, the fluid may be a body fluid such as serum, urine, cerebrospinal fluid, pleural fluid or the like. Alternatively, the fluid may be water, saline or any appropriate buffer, or mixtures of body fluids and other fluids may be used.

A single stage assay system, as will first be described, in general consists of an analyte, an antianalyte, C1 and a substrate to be modulated by C1 to provide a detectable signal. Means to inhibit nonimmune activation of C1 may be provided. In a multistage amplification assay system, as will subsequently be described, a substrate initiates a sequence of catalytic reactions leading to a detectable signal. The analyte, antianalyte, C1 and substrate may be combined in the assay fluid at the beginning of the assay procedure, or they may be added individually or in any combination and in any sequence. It is understood that the order in which the elements are described in detail below is not to be construed as limiting the assay method to that particular order.

The analyte may be from any source, and may be an antigen, an antibody or a hapten. For example, the analyte may be an antigen present in a body fluid, or it may be isolated from a body fluid and subsequently introduced into a different fluid, such as buffer. In other cases, the analyte may be from a source other than a body fluid, as, for example, a culture of microorganisms or a cellular extract thereof. If the analyte is a hapten, it may be necessary to render it antigenic before it can be detected or determined by the method of the invention. Methods to render haptens antigenic are well-known to those skilled in the art, and no further details in this regard are considered to be necessary for a complete understanding of the invention.

An antianalyte is contacted with the analyte in the fluid to induce the immunological reaction. The antianalyte may be an antigen or an antibody, or it may be any appropriate analogue thereof which reacts specifically with the analyte. In addition, the antianalyte may be an antibody fragment or an antibody complex consisting of a plurality of bound antibodies, as, for example, a second antibody bound specifically to a first antibody. Alternatively, the analyte may bind to several different antianalytes at once, for example, an ensemble of polyclonal antibodies or a mixture of several monoclonal antibody molecules which bind simultaneously to different surface areas of the analyte. Generally, the second antibody is raised against the first antibody in a different species. The plurality of bound antibodies in the complex may contain from two to about ten antibodies.

The quantity of antianalyte to be used may be varied over a wide range. A limited amount of antianalyte having insufficient binding sites to bind all of the analyte may be used wherein the analyte binds to the antianalyte in proportion to its concentration in the fluid. In another type of assay, excess antianalyte having sufficient binding sites to bind essentially all of the analyte is used.

The fluid containing the analyte and antianalyte may be incubated, if necessary, to induce binding. Incubation may be carried out at any temperature and for any length of time suitable to facilitate binding, preferably from about 20° to 40° for about 1 minute to 4 hours. Antianalyte and analyte which are bound are hereinafter referred to as the bound fraction and antianalyte and analyte which do not bind are hereinafter referred to as the free fraction. The assay may, but need not, be carried out in such a way that equilibrium is established between the bound and free fractions.

C1 is added to the assay medium in any suitable form as, for example, as part of complement or any portion thereof, or it may be in serum. Preferably, C1 is separated from the other complement proteins and may, if desired, be purified prior to addition. Methods to prepare complement and isolate C1 therefrom are well-known to those skilled in the art and no further details in this regard are needed for a full understanding of the invention.

As mentioned above, C1 consists of three subcomponents, designated C1q, C1r and C1s. C1q is an organizing protein which contains multivalent binding sites for the Fc portion of certain immunoglobulins as well as binding sites for the C1r and C1s subcomponents. C1r and C1s are unactivated enzymes, generally referred to as zymogens. C1 remains inactive until a complex consisting of C1 and a bound fraction is formed by a binding reaction between C1q and the Fc portion of an appropriate antibody. The order of binding is not important. C1 may bind to a bound fraction, or it may bind to the antibody prior to the immunological reaction. If desired, a separate incubation step may be carried out to facilitate binding of C1 to the antibody or the bound fraction.

Activation of C1 upon formation of a C1:antianalyte:analyte complex occurs sequentially beginning with C1q. A conformational change induced in C1q by formation of the complex is transmitted structurally to C1r, thereby triggering activation of C1r to C1r-ac. (An activated component is hereinafter indicated by the notation ac following the designation of the component.) C1r-ac cleaves a peptide bond in C1s to produce C1s-ac.

C1s-ac modulates a substrate present in the assay medium to give a detectable signal. Exemplary of suitable substrates are chromogens, such as the p-nitrophenyl esters of N-(benzyloxycarbonyl)-L-tyrosine and N-(tert-butyloxycarbonyl)-L-lysine which undergo a color change on reaction with the active enzyme; fluorogens, such as N-(tert-butyloxycarbonyl)-L-leucyl-glycyl-L-arginine methylcoumarinyl amide, (protected AMC), which are converted to fluorescent materials; or substrates, such as N-(benzyloxycarbonyl)-L-alanyl-L-arginine thiobenzyl ester, which may be detected by an indirect chromogenic system.

The means for signal detection of course depends on the substrate used. If the signal is a color change, it may be detected visually or with a colorimeter or a spectrophotometer. Fluorescence omission is conveniently measured with a fluorimeter. Either kinetic or thermodynamic measurements may be made. Kinetic measurements determine the rate of change which occurs over a period of time, and are generally carried out by making a series of measurements at various times after combining the assay reagents. Thermodynamic measurements determine the extent of change which has occurred when equilibrium has been reached between substrate and reaction product. Procedures for detection or quantitative measurement of the signal are well-known in the art, and further details in this regard are not necessary for a complete understanding of the invention.

In some cases, it may be desirable to provide means for inhibition of nonimmune activation of C1. Nonimmune activation may be caused by numerous substances such as viruses, bacteria or protein carbohydrates, or it may occur by physical changes in the assay medium, such as changes in temperature, pH, reagent concentrations and the like, or it may occur by spontaneous autoactivation. Various methods are known to inhibit nonimmune activation of C1, and any suitable method may be used. Exemplary of useful methods are addition to the assay medium of a naturally occurring C1 inhibitor (C1-INH) or a chemical modification thereof, by addition of a synthetic C1 inhibitor such as nitrophenyl guanidinobenzoate, or by addition of divalent cations such as ions of calcium, manganese and cobalt. Preferred inhibitors of nonimmune C1 activation are C1-INH, calcium ions, or mixtures thereof in total concentrations of 5 mM or higher whereby nonimmune (auto) activation, but not immune activation, is inhibited. The use of calcium is described by Lin et al. in *J. Biol. Chem.* 255, 7756 (1980).

A preferred embodiment of the invention is a multistage complement-induced cascade amplification assay wherein a substrate reacts to induce a sequence of reactions leading ultimately to a detectable product. In describing this embodiment of the invention, it is convenient to consider C1s-ac as a first enzyme which enzymatically modulates a substrate to a modulator for a second reaction, such as a second enzyme or an enzyme derivative, such as a coenzyme, inhibitor, precursor, activator or cofactor, which provides a signal or which reacts with a third modulator to provide a signal. C1s-ac or any subsequent enzyme may also react with more than one substrate or modulator to provide additional enzymes or enzyme derivatives which may continue the cascade of enzymatic reactions until a detectable signal is generated. By proper selection of substrates to be added to the assay medium, any desired number of amplification stages may be carried out.

It is evident that amplification occurs because C1s-ac and the subsequently formed enzymes or enzyme derivatives act as true catalysts wherein a single molecule may act on an essentially unlimited number of substrate molecules without itself being consumed. Thus, in theory, one molecule of C1s-ac would be sufficient to perform the method of the invention. In practice, determination of the amount of C1 to be added and the number of amplification stages to be used are well within the purview of one of ordinary skill in the art.

In a cascade assay, any substrate may be used which reacts with C1s-ac to give a modulator for a second reaction which can continue the cascade. Preferred substrates are peptides, most preferably peptides of 5 or less amino acid residues containing an arginine residue in the position adjacent the site where C1s-ac reacts and optionally containing suitable protecting or modifying groups.

In another embodiment of the invention, the immunological reaction of the invention is carried out on the surface of a solid support. As known in the art, the solid support may be any support which does not substantially interfere with the assay. Exemplary of solid supports which may be used are glass and polymeric materials, such as polyethylene, polystyrene and the like. Such supports may be fabricated into any suitable shape, such as sheets, plates, wells, or preferably, tubes. For example, the immunological reaction may be carried out on the inside walls and bottom of a tube, preferably a plastic tube with one closed end. Attachment of the antianalyte to the solid support may be carried out by any conventional procedure, such as, for example, absorption or covalent bonding. These procedures are well-known in the art.

The bound fraction consisting of analyte and antianalyte on the surface of the solid support may activate C1 as described above. In other cases, the solid support may interfere with the activation of C1. In such cases, the asay is preferably performed by a sandwich technique wherein the analyte bound to the supported antianalyte is further bound to an antibody recognizing a second determinant on the analyte. The antianalyte:analyte:antibody sandwich thus formed activates C1.

All embodiments of the method of the invention are suitable for either detection of an analyte or determination of its concentration. Analyte concentration may be determined by comparing the magnitude of the signal with the magnitude of the signal measured upon assay of a range of known quantities of the analyte assayed under essentially identical conditions.

In accordance with another aspect of the invention, there is provided a reagent kit or package of materials for accomplishing an assay for an analyte in accordance with the method of the invention. The kit may include an antianalyte, optionally attached to a solid support, and complement or a complement fraction which includes the first component. The kit may also includes the standards for the analyte, as, for example, one or more analyte samples of known concentration, or it may include other reagents, such as a substrate or other labeled or unlabeled specific antigens, antibodies or complexes thereof useful in carrying out the assay. It may include solutions, such as saline or buffers. The components of the kit may be supplied in separate containers, as, for example, vials, or two or more of the components may be combined in a single container.

The following example is provided to further describe the invention, but is not to be construed in any way as limitative of the invention.

EXAMPLE

Detection of Sheep Red Blood Cells

Sheep red blood cells (SRDC) and rabbit-anti-sheep IgG (Cordis Labs, Miami, Fla.) were combined in gelatin-barbital saline, pH 7.3, and incubated for 30 min. at 37° C. followed by 30 min. at 0° C. to give a suspension containing $1 \times 10^9$ bound cells/ml. In separate tubes, various dilutions of the bound cells were made with the same buffer. To each tube was added sufficient unactivated C1 (*J. Immunology* 125, 390 (1980)) to give a concentration of $7 \times 10^{-9}$ M, and sufficient stock $1.5 \times 10^{-3}$ M protected AMC (Vega Biochemicals, Tucson, Ariz.) solution to give a final dye concentration of $1 \times 10^{-4}$ M. The tubes were incubated for 15 min. at 37° C., centrifuged for 5 minutes at 1000 RPM, and the supernatant from each tube was irradiated with excitation light of 380 nm. Fluorescence emission was determined at 460 nm and inner-filter corrections were applied. The corrected fluorescence data is given in the Figure, and is compared with control data obtained by the same procedure with SRBC (antigen) and TgC (antibody) alone.

It is seen that significant activation of C1 occurs only in the presence of suitable concentration of the antigen-antibody complex. An increase in either antibody or antigen concentration alone did not produce an increase in fluorescence emission.

In summary, the invention is a method and materials for immunoassay of an analyte which take advantage of various properties of C1. Thus, in accordance with the method, C1 is enzymatically inactive until activated by a bound antigen-antibody pair. Once thus activated immunologically, C1 is used enzymatically to modulate a substrate to provide a detectable signal which may, if desired, be quantitatively measured. A homogeneous enzyme immunoassay which avoids conjugation of the enzyme to an immunological component of the assay is thereby achieved. Exceptionally high sensitivity is achieved by a cascade of sequential enzymatic reactions initiated by C1.

What is claimed is:

1. A method for determining the concentration of an analyte in a fluid comprising:
    (a) contacting an analyte in a fluid with an antianalyte, a substrate selected from the group consisting of a chromogen and a fluorogen and the first component of complement;
    (b) causing said analyte to bind to said antianalyte whereby said first component is activated to modulate said substrate and provide a detectable signal;
    (c) measuring said detectable signal; and
    (d) determining the concentration of said analyte in said fluid by comparing the magnitude of said signal with the magnitude of a signal established for a known quantity of said analyte.

2. The method in accordance with claim 1 wherein said fluid is selected from the group of fluids consisting of a body fluid, saline, and a buffer.

3. The method in accordance with claim 1 wherein said analyte is selected from the group of analytes consisting of an antigen, a hapten and an antibody, and said antianalyte is selected from the group of antianalytes consisting of an antigen, an antibody, an antibody fragment, and a bound antibody complex consisting of from two to about ten antibodies.

4. The method in accordance with claim 1 wherein said first component is separated from other components of complement before being added.

5. The method in accordance with claim 1 wherein said first component is in serum.

6. The method in accordance with claim 1 wherein said detectable signal is a color change resulting from modulation of said substrate.

7. The method in accordance with claim 1 wherein said detectable signal is a change in fluorescence emission resulting from modulation of said substrate.

8. The method in accordance with claim 1 wherein said antianalyte is attached to a solid support.

9. The method in accordance with claim 8 further comprising adding an antibody to said fluid whereby said antibody binds to said analyte.

10. The method in accordance with claim 1 further comprising inhibiting nonimmune activation of said first component.

11. A method for detecting an analyte in a fluid comprising contacting an analyte in a fluid with an antianalyte, a substrate selected from the group consisting of a chromogen and a fluorogen and the first component of complement, said analyte binding to said antianalyte to provide a bound fraction, said bound fraction activating said first component, said activated first component modulating said substrate to provide a signal, and detecting said signal to indicate the presence of said analyte in said fluid.

12. A method for determining the concentration of an analyte in a fluid sample comprising:
    (a) contacting an analyte in a fluid with an antianalyte under conditions which provide a mixture including a bound fraction;
    (b) adding the first component of complement;
    (c) inhibiting nonimmune activation of said first component so that said first component is activated by said bound fraction;
    (d) adding to said mixture a substrate selected from the group consisting of a chromogen and a fluorogen wherein said substrate is modulated by said activated first component and provides a detectable signal;
    (c) measuring said detectable signal; and
    (f) determining the concentration of said analyte in said fluid by comparing the magnitude of said signal with the magnitude of a signal established for a known quantity of said analyte.

13. A method for determining the concentration of an analyte in a serum sample comprising:
    (a) contacting an analyte in a serum sample, which includes complement, with an antianalyte and a substrate selected from the group consisting of a chromogen and a fluorogen;
    (b) causing said analyte to bind to said antianalyte to give a bound fraction so that said bound fraction activates the first component of said complement, and said activated first component modulates said substrate and provides a detectable signal;
    (c) measuring said detectable signal; and
    (d) determining the concentration of said analyte in said serum sample by comparing the magnitude of said signal with the magnitude of a signal established for a known quantity of said analyte.

14. The method in accordance with claim 13 further comprising inhibiting nonimmune activation of said first component.

15. The method in accordance with claim 13 wherein said antianalyte is attached to a solid support.

* * * * *